United States Patent [19]

Millen

[11] Patent Number: 6,129,709
[45] Date of Patent: Oct. 10, 2000

[54] ADJUSTABLE SUPPORT SYSTEM

[76] Inventor: Thomas H. Millen, 4272 Wellwynd Ct., Palm Harbor, Fla. 34685

[21] Appl. No.: 09/118,429

[22] Filed: Jul. 17, 1998

[51] Int. Cl.[7] .................................................. A61M 5/32
[52] U.S. Cl. ........................................ 604/179; 604/345
[58] Field of Search .................................. 604/174, 179, 604/327, 345, 353; 128/DIG. 15, DIG. 26; 224/224, 226, 258, 148, 191

[56] References Cited

U.S. PATENT DOCUMENTS

| | | |
|---|---|---|
| 3,812,851 | 5/1974 | Rodriguez . |
| 4,134,404 | 1/1979 | Williams, Jr. . |
| 4,511,358 | 4/1985 | Johnson, Jr. et al. ................. 604/327 |
| 4,582,508 | 4/1986 | Pavelka .................. 604/179 |
| 5,234,420 | 8/1993 | Horton et al. ........................... 604/345 |
| 5,244,464 | 9/1993 | Maden et al. . |
| 5,415,183 | 5/1995 | Somers . |
| 5,515,866 | 5/1996 | Somers . |
| 5,672,159 | 9/1997 | Warrick . |
| 5,716,344 | 2/1998 | Kiel ......................... 604/174 |
| 5,728,070 | 3/1998 | Walker et al. .......................... 604/179 |
| 5,776,105 | 7/1998 | Corn ....................... 604/174 |

OTHER PUBLICATIONS

Advertisement, *American Journal of Nursing*, Jul. 1998, vol. 98, No. 7.

*Primary Examiner*—Mark O. Polutta
*Assistant Examiner*—David J. Cho
*Attorney, Agent, or Firm*—Joy L. Bryant; Bart A. Singer

[57] ABSTRACT

The present invention uses straps and fasteners to adjustably support a receptacle on a patient who is recovering from a surgery or wound. Drainage from the wound or surgical incision is directed into the receptacle, which is fastened to a primary strap in any position that is convenient and comfortable for the patient. The extensive adjustability of the system facilitates prompt patient ambulation by allowing the patient to locate the receptacle in a position that maximizes comfort and minimizes personal inconvenience.

2 Claims, 9 Drawing Sheets

ADJUSTABLE SUPPORT SYSTEM

FIELD OF THE INVENTION

The present invention relates generally to supports and straps for medical devices. More particularly, the invention relates to adjustable support systems for carrying receptacles that contain bodily fluids.

BACKGROUND OF THE INVENTION

After many types of surgical procedures are performed, excess fluids must be drained from the patient, usually directly from a wound or incision. The fluid drains through tubes into a receptacle or bag. The tubes may or may not be stitched into the wound or incision. Frequently, a suction reservoir is used as the receptacle. A suction reservoir is an elastic container that receives bodily fluids from a drainage tube. When squeezed a suction reservoir ejects its contents and creates a partial vacuum that tends to draw the fluid to be drained into the suction reservoir. The typical drainage receptacle has a short tab and possibly a spring clip for attaching the receptacle to some support. The receptacle often is clipped or safety pinned to the bandage that closes the wound or incision, to the patient's hospital gown, or to any convenient support.

Doctors and nurses typically attach the receptacle to a place where it can be found and monitored easily. Even a particularly empathetic caregiver has trouble optimizing the location of the receptacle to minimize discomfort for any particular patient. Sometimes additional tape or a bandage is applied to the patient just to provide a support to which the receptacle can be clipped. Some patients are allergic or have sensitivities to various tapes and bandages. However, after having undergone surgery, most patients usually tolerate whatever the healthcare practitioners do with the drainage receptacle. Depending upon the details of the surgery and the patient's recovery therefrom, the drainage receptacle might be used for periods of time ranging from hours to several weeks. The longer the duration of the drainage requirement, the more bothersome the drainage receptacle becomes to the typical patient. Bathing or showering becomes a complicated chore. The increasing trend toward outpatient surgery and early hospital release from inpatient surgery has created the need for a patient-oriented post-surgery drain support system. In addition, for the longer drainage periods, when the patient is trying to recover and assimilate into society, hiding the receptacle from others when in public is unduly difficult. Until the present invention, these problems were unrecognized because the drainage bottle and its support were considered an integral part of the surgery, something that the patient needed to tolerate. To address these problems, the present invention discloses a system of supports for a receptacle that is easily adjustable by the patient.

The need for a patient-friendly device to support a drainage receptacle will be felt more urgently as hospital stays become shorter and the likelihood increases that the patient will be required to continue using the drainage receptacle at home, after being released from the hospital. Home recovery offers the patient both opportunities and challenges to healing. The present invention shifts the process of finding a convenient and comfortable place to mount the receptacle from being a challenge to being an opportunity for added comfort and control of the healing process.

SUMMARY OF THE INVENTION

The present adjustable support system generally comprises a primary strap and a receptacle fastener affixed to the primary strap. A receptacle is affixed to the primary strap by the receptacle fastener. Preferably, the receptacle is used for medical purposes and is typically a drainage receptacle that drains fluid from a surgical incision or wound in a patient. In use, the primary strap is hung on the user and the receptacle is affixed to the primary strap in any position that is convenient and comfortable for the patient. Further stability of the support system is achieved by the inclusion of additional straps and fasteners. The extensive adjustability of the system facilitates prompt patient ambulation by allowing the patient to locate the receptacle in a position that maximizes comfort and minimizes personal inconvenience. Prior approaches for supporting medical receptacles on patients typically did not consider patient comfort and convenience as critical design considerations.

The present invention addresses a number of important issues that have not been successfully resolved by prior approaches.

A first object of the invention is to provide a comfortable and convenient support system for a medical receptacle. The support system should be easy to don, remove, and adjust by a patient that uses the system or his/her caregiver.

A second object is that the support system allows the patient to shower safely. An important aspect of this object is that the system should not encumber either of the patient's hands or legs. Free-hand ambulation is an important safety benefit.

A further object of the invention is that it be maximally adjustable. All patients are different and slight variations in adjustments to the support system can greatly reduce patient discomfort.

Another object of the invention is to eliminate the need to apply a bandage or dressing to a patient for the sole purpose of attaching a drainage receptacle.

A further object of the support system is that it be provided with sufficient optional supports to prevent the receptacle from being dislodged or uncomfortably shifted, even while the patient sleeps.

Another object of the invention is that it be capable of being concealed under the patient's clothing.

A further object of the support system is that it minimizes patient contact with metal pins and clips.

Another object of the invention is that it be provided in appropriate sizes.

Additional objects and advantages of the invention will be set forth in part in the description that follows, and in part will be obvious from the description, or may be learned by practice of the invention. The objects and advantages of the invention will be obtained by means of instrumentalities in combinations particularly pointed out in the appended claims.

BRIEF DESCRIPTION OF THE DRAWINGS

The accompanying drawings illustrate a complete embodiment of the invention according to the best modes so far devised for the practical application of the principles thereof, and in which:

In FIGS. 3A, 3B, and 3C, the width and especially the thickness of the primary strap have been greatly expanded relative to the length of the primary strap so that details can be seen more clearly.

In FIGS. 5A, 5B, and 5C, the width and especially the thickness of the waist strap have been greatly expanded relative to the length of the waist strap so that details can be seen more clearly.

In FIGS. 7A, 7B, and 7C, the width and especially the thickness of the stabilization strap have been greatly expanded relative to the length of stabilization strap so that details can be seen more clearly.

DETAILED DESCRIPTION OF PREFERRED EMBODIMENTS

Figure 1A:
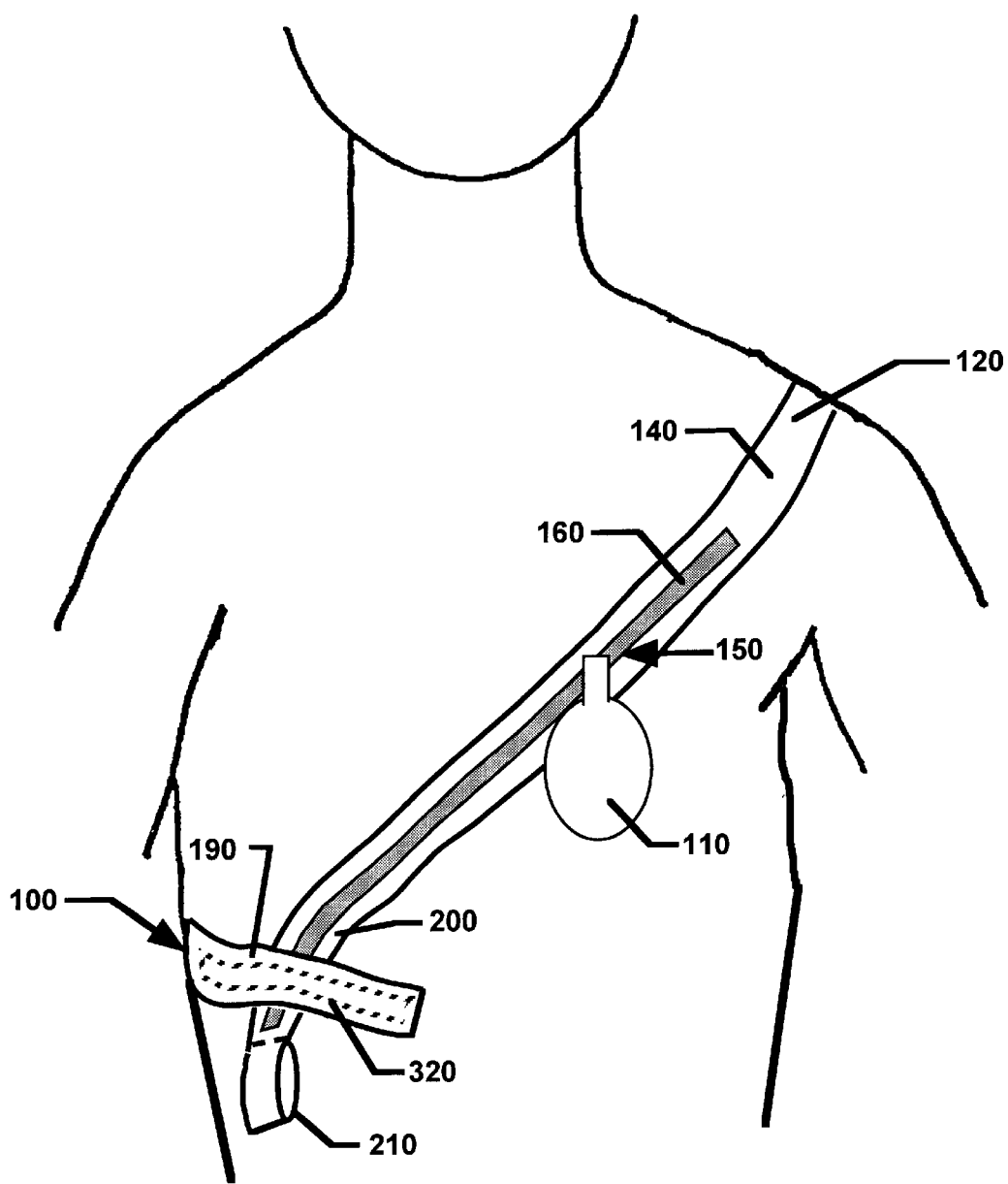
FIG. 1A shows an anterior view of a primary strap worn on a patient with a receptacle attached thereto.
Figure 1B:
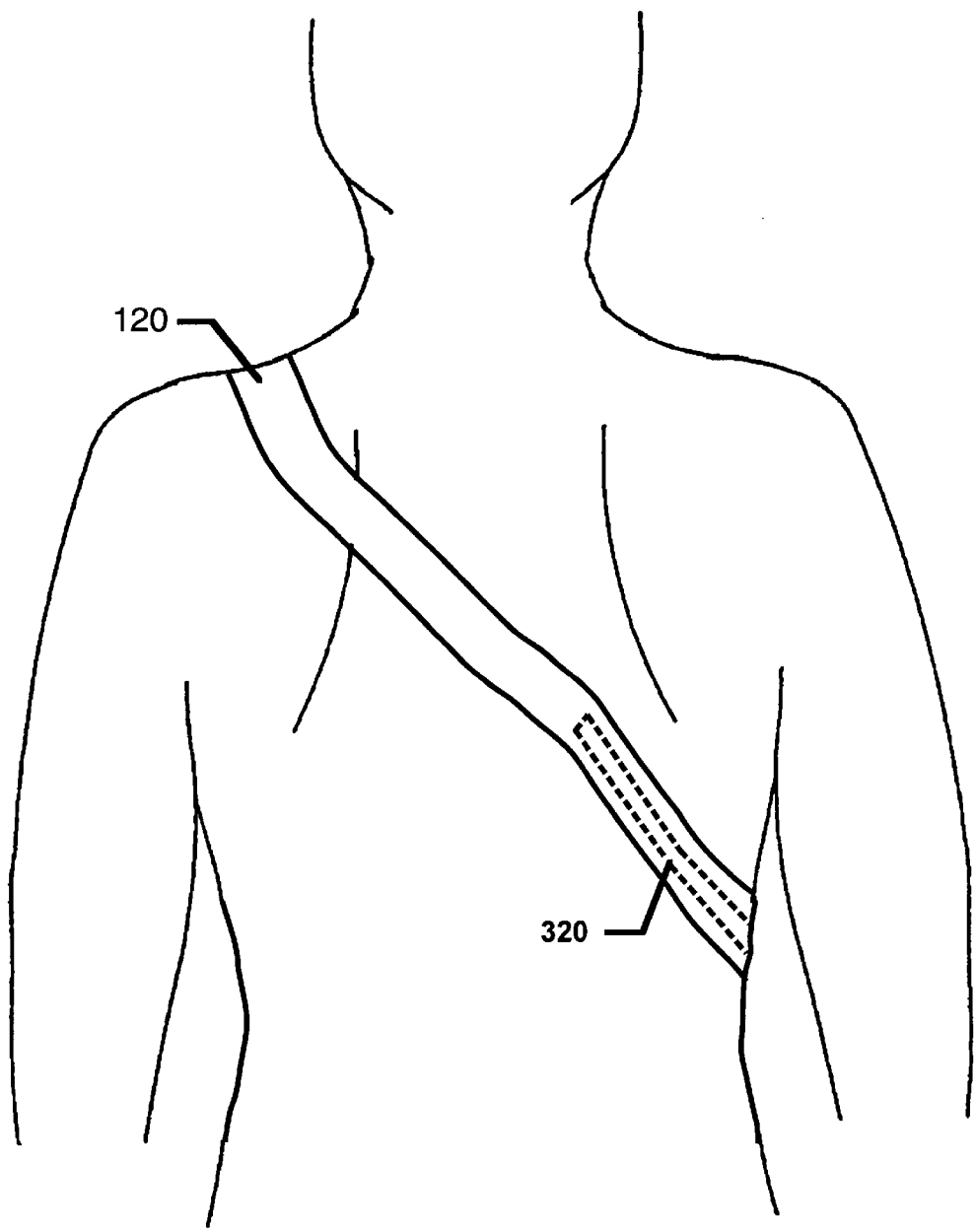
FIG. 1B shows a posterior view of a primary strap worn on a patient.
Figure 2:
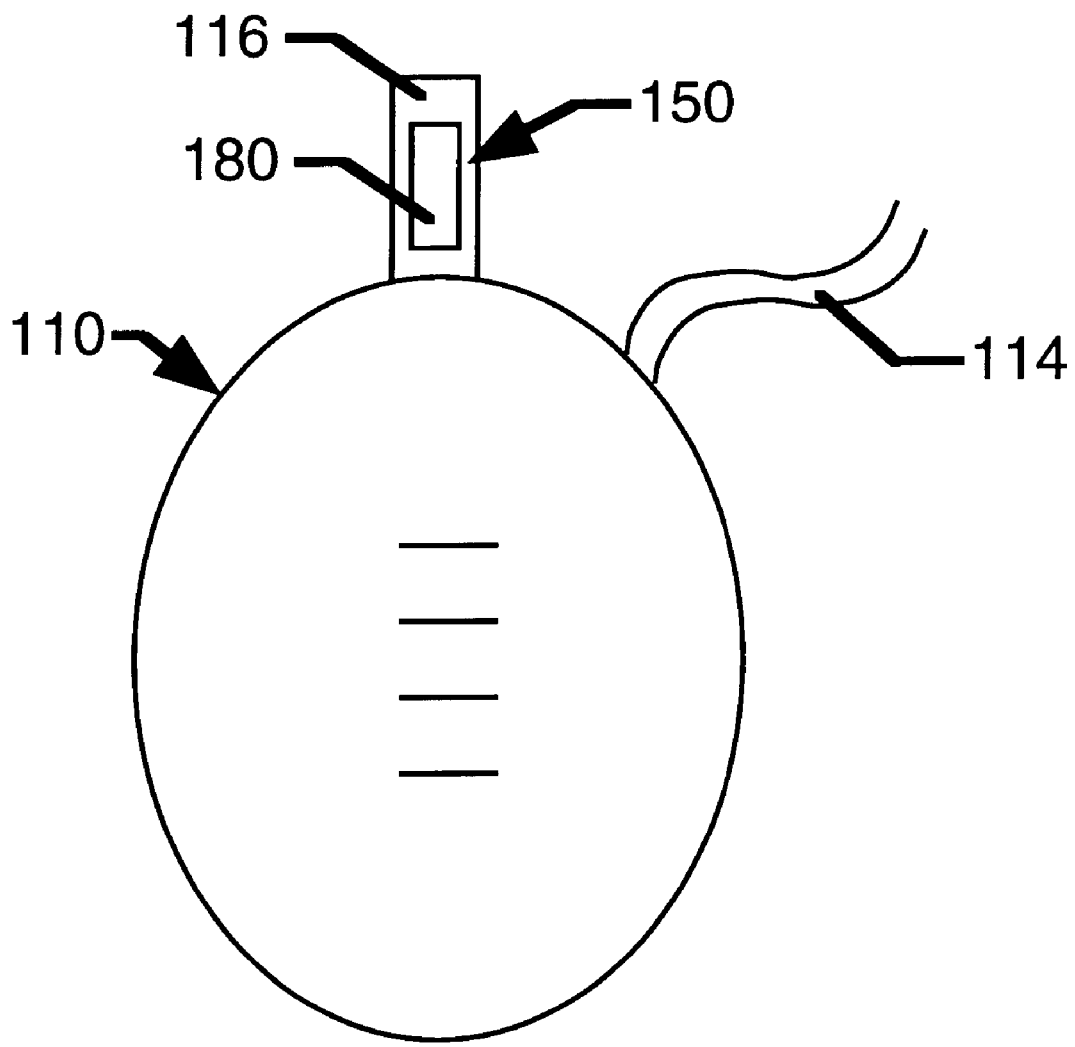
FIG. 2 illustrates a typical drainage receptacle with loop material mounted on the receptacle tab to serve as part of a receptacle fastener.

The simplest embodiment of an adjustable support system 100 for supporting a receptacle 110 is shown in FIGS. 1A and 1B. The adjustable support system 100 includes a primary strap 120 that supports the receptacle 110 through the use of a receptacle fastener 150. Although the generic term "receptacle" is used in conjunction with the invention as it is described below, the preferred receptacle is a medical receptacle. In circumstances in which the receptacle 110 is to be explicitly restricted to medical uses, it will henceforth be referred to as a medical receptacle. A typical medical receptacle used for draining wounds and incisions is shown in FIG. 2, although other types of medical receptacles are usable in conjunction with the invention. In FIG. 2, a drainage tube 114 directs material into the receptacle 110, which includes a receptacle tab 116 for facilitating fastening to the receptacle fastener 150. Any suitable fastener is used as the receptacle fastener 150. For example, the receptacle fastener 150 comprises one or more snaps, clips, pins, buckles, safety pins, zippers, or various types of permanent and non-permanent adhesives. Although the receptacle fastener 150 preferably fastens to the receptacle tab 116, alternate embodiments of the invention permit the receptacle fastener 150 to fasten to other portions of the receptacle 110.

In the preferred embodiment of the invention, hook-and-loop fastener material is used as the receptacle fastener 150. (Hereafter, the hook portion of hook-and-loop fastener material will be referred to as hook material and the loop portion as loop material.) In the most preferred embodiment of the invention, a strip of hook material is affixed to the primary strap outward-facing side 140 and is called the primary strap strip of hook material 160. Because the primary strap outward-facing side 140 typically does not come in contact with a user's skin, it is well suited for receiving the primary strap strip of hook material 160, which is generally stiff and prickly and would be uncomfortable if it were to be in contact with the user's skin. Therefore, in the preferred embodiments of the invention, the hook portion of any hook-and-loop fastener material is directed away from the user's skin, while the loop portion, which is generally soft and fuzzy is directed towards the user's skin. In the case of the receptacle fastener 150, FIG. 2 shows that the loop material is attached to the receptacle 110, and is called a receptacle strip of loop material 180.

In general, the primary strap 120 is hung on the user's body, usually by draping the primary strap 120 along a path around a portion of the user's body. In the embodiment of the adjustable support system 100 shown in FIGS. 1A and 1B, the primary strap 120 is draped along a path that extends over a shoulder of the user and around the user's trunk. The primary strap 120 is used equally well over either shoulder and is also wearable such that the receptacle is supported on the user's back or side, rather than the front of the user. To secure the primary strap 120, a primary strap self-fastening means is required to fasten a first portion 190 of the primary strap 120 to a second portion 200 of the primary strap 120 so as to form a closed loop that encircles the user. Many different types of fasteners, such as pins, safety pins, buckles, hook-and-eye hangers, D-type adjusters, snaps, clips, and zippers are suitable as the primary strap self-fastening means. In the preferred embodiments of the invention, hook-and-loop fastener material is used as the primary strap self-fastening means. Details of the most preferred embodiment are shown more clearly in FIGS. 3A, 3B, and 3C, where a primary strap strip of loop material 170 is affixed to the primary strap inward-facing side 130 on the first portion 190 of the primary strap 120. The primary strap strip of loop material 170 on the first portion 190 of the primary strap 120 cooperates with the primary strap strip of hook material 160 affixed to the second portion 200 of the primary strap 120 to fasten the first and second portions of the primary strap 120 together and form the closed loop around the user. In these embodiments of the invention, the primary strap strip of hook material 160 serves as a cooperating portion of both the receptacle fastener 150 and the primary strap self-fastening means.

Figure 3A:
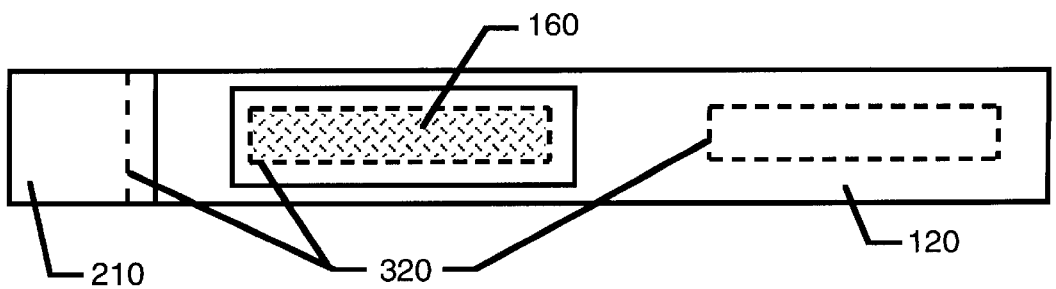
FIG. 3A shows the primary strap outward-facing side (away from the patient's skin).
Figure 3B:
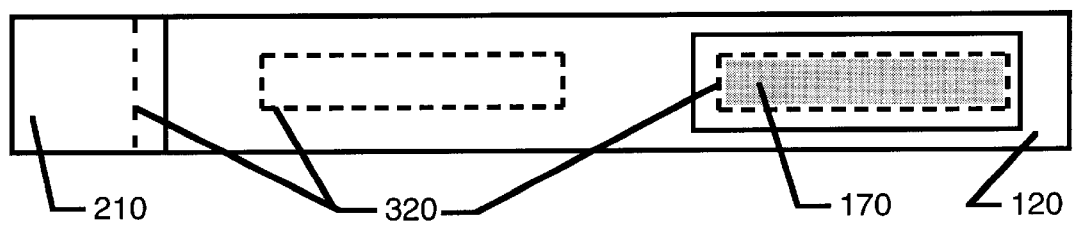
FIG. 3B shows the primary strap inward-facing side (adjacent the patient's skin).

In FIG. 3A, the primary strap outward-facing side 140 is shown. On the right side of the figure, stitching 320 secures the primary strap strip of loop material 170 to the primary strap 120. In the left-central region of the primary strap 120 the primary strap strip of hook material 160 is stitched 320 through the material. Conversely, in FIG. 3B, the stitching 320 through the primary strap strip of loop material 170 is shown on the right and only the stitching 320 that secures the primary strap strip of hook material 160 to the primary strap 120 is shown in the left-central region. Although both the primary strap strip of hook material 160 and the primary strap strip of loop material 170 are shown about equal length in the figures, in practice, the primary strap strip of hook material 160 typically extends about 24 inches in length while the primary strap strip of loop material 170 extends about 13 inches in length. The longer length of the primary strap strip of hook material 160 provides more adjustability in the placement of the receptacle 110 on the primary strap strip of hook material 160. The distance between the primary strap strip of hook material 160 and the primary strap strip of loop material 170 is sized to obtain a preferred size of the primary strap 120.

Sizing of the primary strap 120 is important for proper comfort and concealment of the device under clothing. Suitable lengths for the primary strap 120 generally range from about 40 inches to about 80 inches.

The width of the primary strap 120 is about 1 inch. This size is large enough to spread the weight, but small enough to conceal under clothing.

Figure 4A:
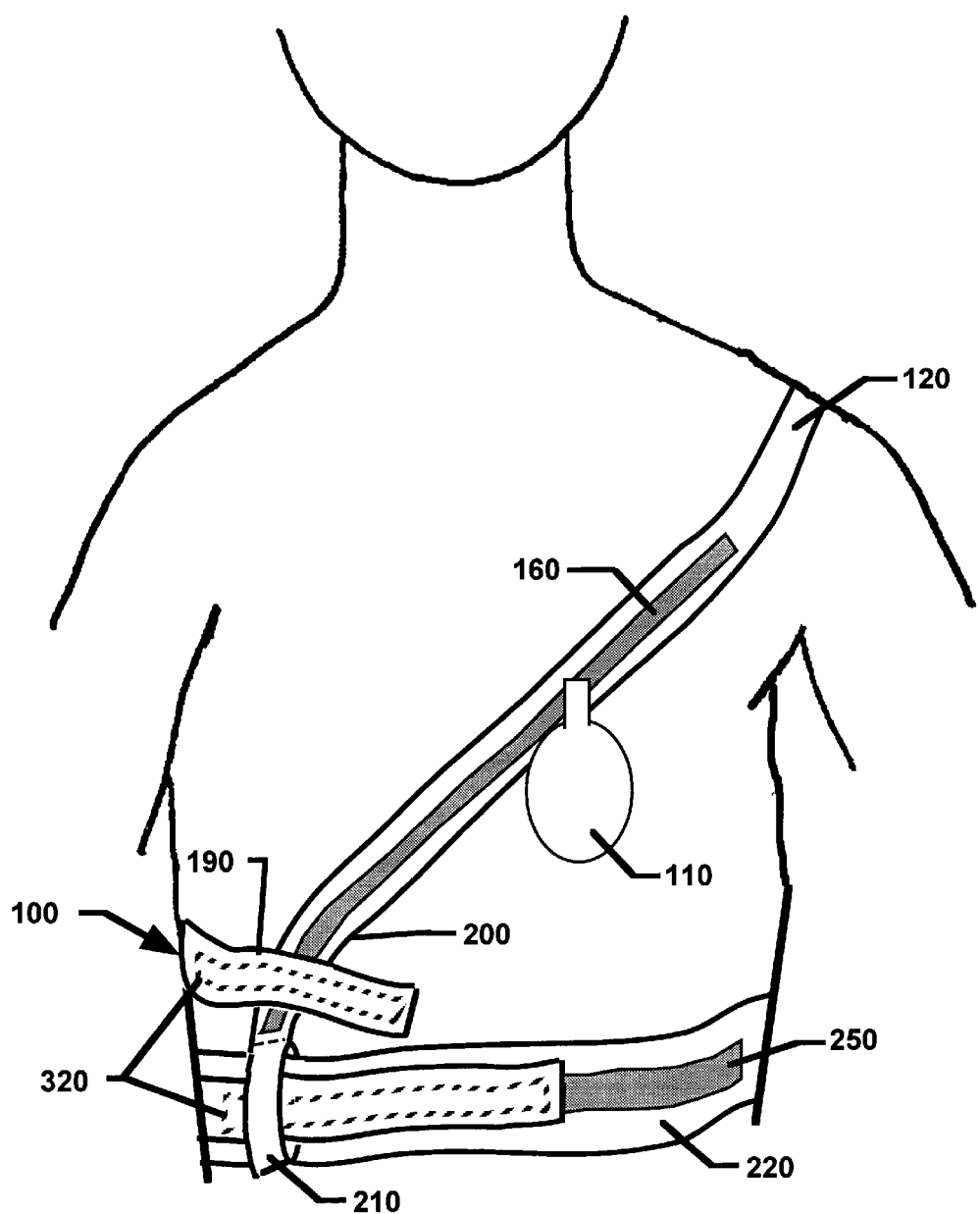
FIG. 4A illustrates an anterior view of an embodiment of the invention that includes a primary strap and a waist strap as worn on a patient with a receptacle attached thereto.
Figure 4B:
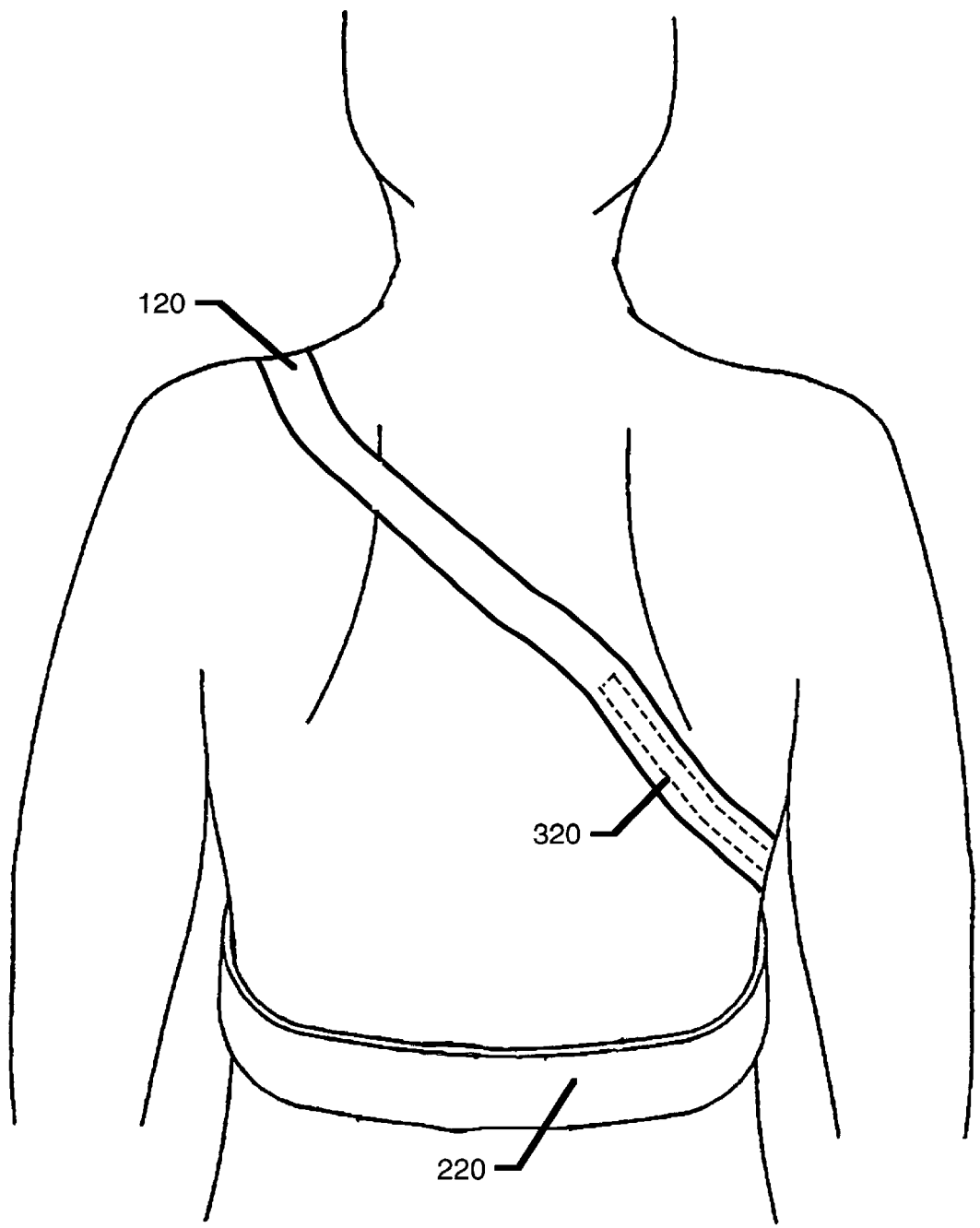
FIG. 4B illustrates a posterior view of an embodiment of the invention that includes a primary strap and a waist strap as worn on a patient.
Figure 5A:
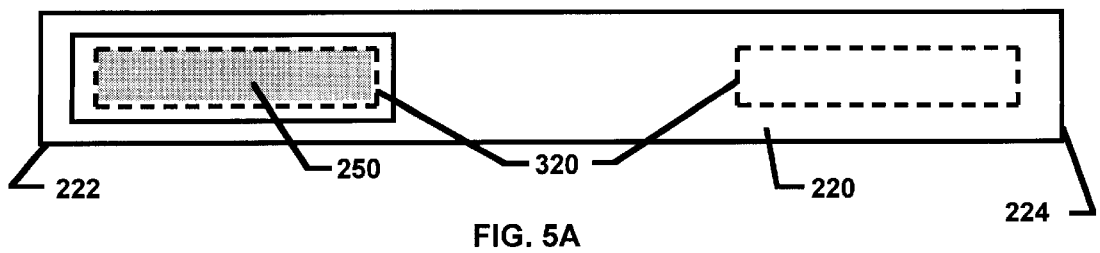
FIG. 5A shows the waist-strap outward-facing side (away from the patient's skin).
Figure 5B:
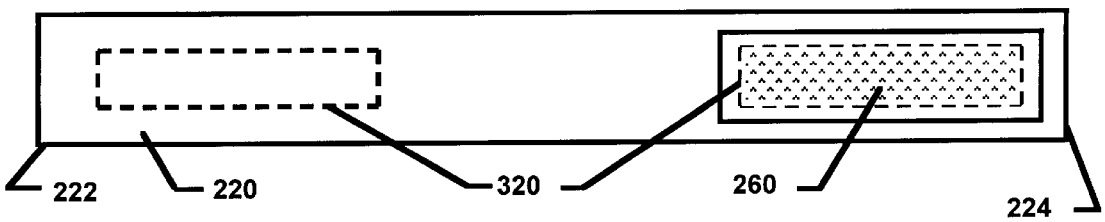
FIG. 5B shows the waist-strap inward-facing side (adjacent the patient's skin).
Figure 5C:
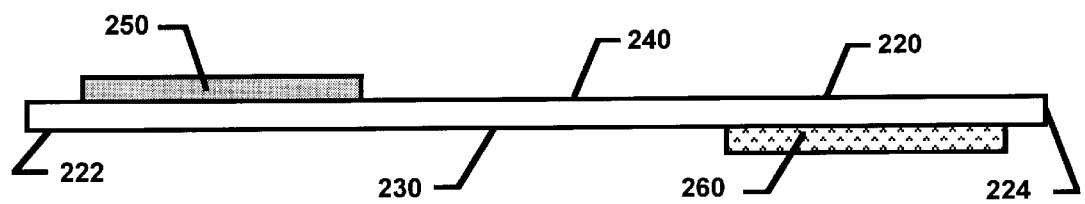
FIG. 5C shows a side view of the waist strap.

Another embodiment of the invention is illustrated in FIGS. 4A and 4B where a waist-strap loop 210 is included in the primary strap 120 and a waist strap 220 passes through the waist-strap loop 210 and encircles the user. Details of the waist strap 220 are shown in FIGS. 5A, 5B, and 5C. A waist-strap self-fastening means secures a first end 222 of the waist-strap 220 to a second end 224 of the waist strap 220. As with the primary strap, 120, multiple types of fasteners are available for this purpose, including: pins, safety pins, buckles, hook-and-eye hangers, D-type adjusters, snaps, clips and zippers. The preferred waist-strap self-fastening means includes a waist-strap strip of hook material 250 affixed to the waist-strap outward-facing side 240 on the first end 222 of the waist strap 220 and a waist-strap strip of loop material 260 affixed to the waist-strap inward-facing side 230 on the second end 224 of the waist strap 220. The right and left orientation of the waist strap 220 is arbitrary and is changeable by reversing the top and bottom edges of the waist strap 220 while maintaining the inward-facing direction of the waist-strap inward-facing side 230.

As with the primary strap 120, proper sizing of the waist strap 220 helps maintain a proper fit, increases user comfort, and facilitates concealment of the adjustable support system 100. Suitable lengths for the waist strap 220 range from about 30 to about 70 inches. A width of about 1-inch is sufficient for most users.

Some details of the preferred construction of the waist strap 220 are shown in FIGS. 5A, 5B, and 5C. In FIG. 5A, stitching 320 attaches the waist-strap strip of loop material 260 to the waist-strap inward-facing side 230 and is shown on the right. The waist-strap strip of hook material 250 is stitched to the waist-strap outward-facing side 240, shown on the left. The situation is reversed in FIG. 5B. Because both the waist-strap strip of loop material 260 and the waist-strap strip of hook material 250 generally only serve to form a waist-strap self-fastening means, they are usually the same length. Lengths of about 13 inches are usually appropriate. Typically, 0.25 inches of extra length of the waist strap 220 extends beyond the ends of the strips of hook-and-loop fastener material. The distance between the waist-strap strip of hook material 250 and the waist-strap strip of loop material 260 is sized to fit the chosen length of the waist strap 220.

Although some users of the adjustable support system 100 may find the waist strap 220 unnecessary, some may prefer to use the waist strap 220 either all of the time or some of the time. In particular, the use of the waist strap 220 at night helps prevent unconscious large excursions of the receptacle 110 when the user is sleeping and possibly shifting position.

Figure 3C:
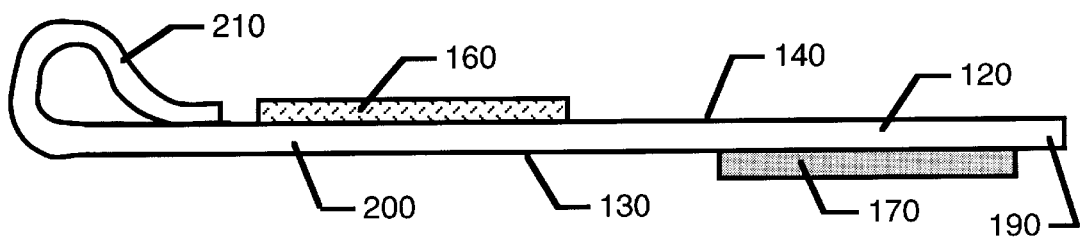
FIG. 3C shows a side view of the primary strap.

The waist-strap loop 210 shown in FIGS. 1A, 3A, 3B, 3C, and 4A is the preferred means for adjustably connecting the primary strap 120 to the waist strap 220. Typically, the waist-strap loop 210 is sized to just barely permit a 1.5 inch wide strap to pass therethrough. This size waist-strap loop 210 smoothly passes a 1.0 inch wide waist strap 220 without permitting excessive play. The waist-strap loop 210 is typically made by folding over an end portion of the primary strap 120, and securing the fold, usually by stitching. Other means known to those skilled in the art for forming the waist-strap loop 210 may also be used. In the most-preferred embodiment, the waist-strap loop 220 is made by folding over an end portion of the primary strap 120 such that the primary strap outward-facing side 140 is brought in contact with itself before securing the fold. This embodiment is shown in FIG. 3C. The primary strap 120 is folded such that the primary strap outward-facing side 140 contacts itself and the discontinuity in thickness occurs away from the user's skin and therefore does not provide a source of patient discomfort. Folding in the opposite direction, such that the primary strap inward-facing side 130 contacts itself, would produce a discontinuous change in thickness that faces the user's skin and could potentially be a source of skin irritation. This situation is highly undesirable. Other suitable means for connecting the primary strap 120 to the waist strap 220 are appropriate. For instance, hook-and-loop fastener material, pins, safety pins, snaps, clips, zippers, buckles, adhesives, or stitching, all provide alternative means for connecting the primary strap 120 to the waist strap 220, although some of those listed allow for little or no adjustability, and most of the alternative means will be less comfortable for the user.

Figure 6:
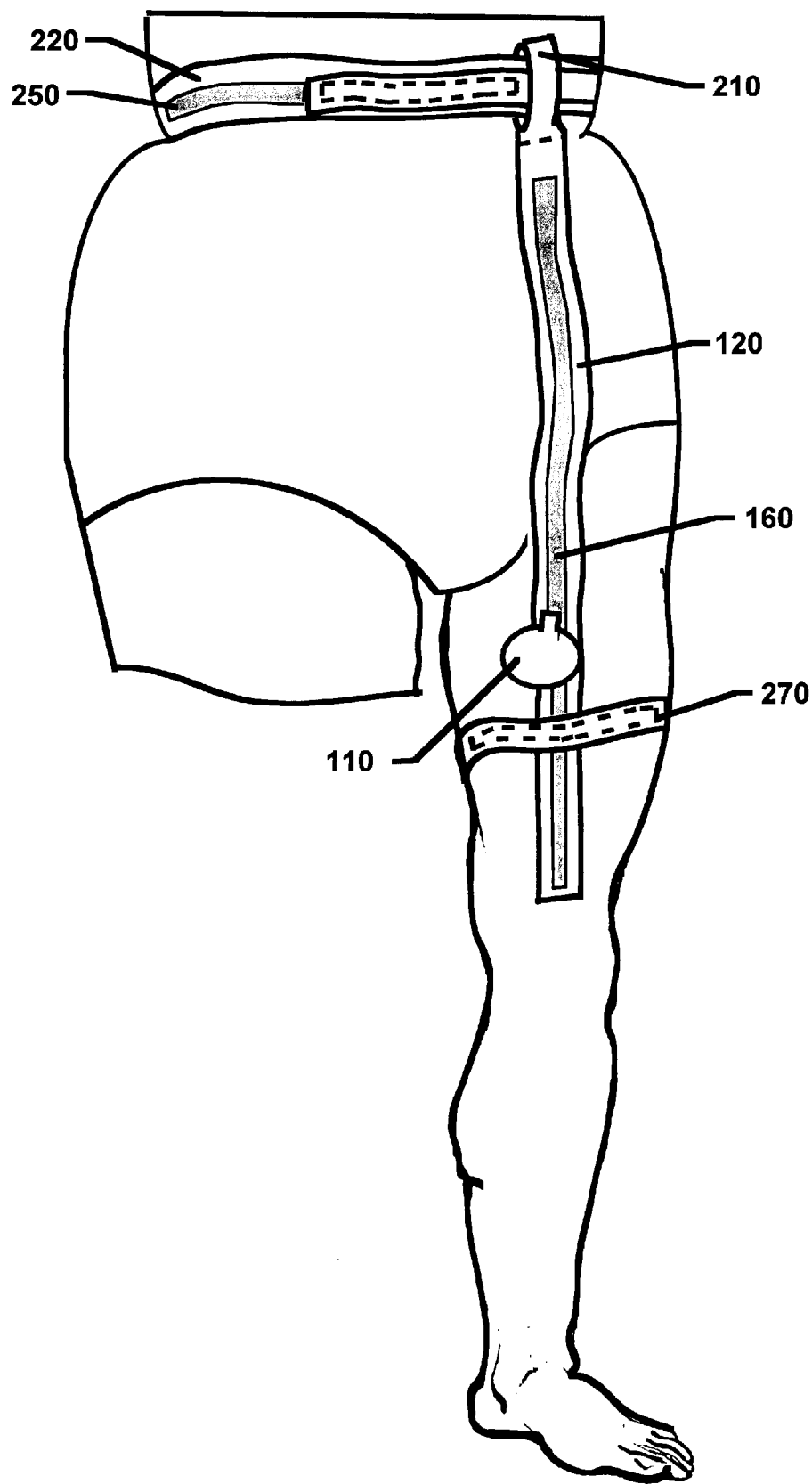
FIG. 6 shows a right-anterior view of an alternate embodiment of the invention in which a waist strap supports a primary strap, and a stabilization strap maintains the primary strap close to the left leg.

An alternate embodiment of the invention is shown in FIG. 6. This form of the invention is appropriate for use when drainage from a wound or incision in the lower portion of a patient's body is required. In FIG. 6, the receptacle 110 is supported along the user's thigh, although in general, the receptacle 110 adjustably fastens anywhere along the length of the primary strap 120. Lengthening the primary strap 120 will allow the receptacle 110 to be located as low as the user's ankle. In most cases, the receptacle 110 need not be placed so low. The use of a suction reservoir or similar device as the receptacle 110 facilitates the drawing of fluid into the receptacle 110, even if the wound or incision is below the height of the receptacle 110. The embodiment of FIG. 6 uses much of the same hardware as the embodiment of FIGS. 4A and 4B. A primary strap 120 is hung on the user by threading a waist strap 220 through a waist-strap loop 210 in the primary strap 120. The waist strap 220 encircles the user's waist and is fastened to itself with a waist-strap self-fastening means as described above. The receptacle 110 is fastened to the primary strap 120 with a receptacle fastener, also as described previously. A stabilization strap 270 is optionally wrapped around both the primary strap 120 and a limb of the user. The use of the stabilization strap 270 reduces jostling of the receptacle 110 and thereby decreases user discomfort. In FIG. 6, the receptacle 110 is fastened to the primary strap 120 above the stabilization strap 270. However, if the situation warrants, fastening the receptacle 110 to the primary strap 120 below the stabilization strap 270 is acceptable. Alternate embodiments of the invention employ multiple stabilization straps 270. The placement of multiple stabilization straps 270 is determined by the user, although one stabilization strap 270 above the receptacle 110 and one stabilization strap 270 below the receptacle 110 is recommended in situations in which multiple stabilization straps 270 are used.

Figure 7A:
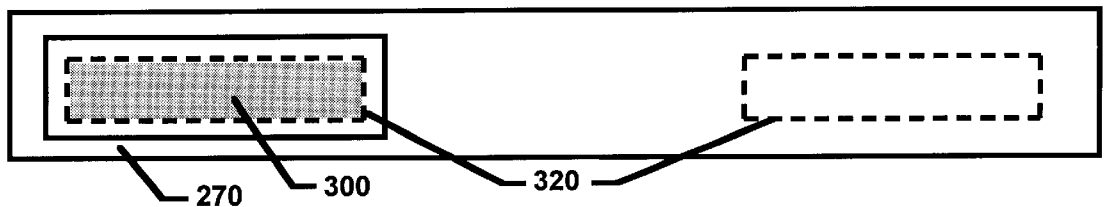
FIG. 7A shows the stabilization-strap outward-facing side (away from the patient's skin).
Figure 7B:
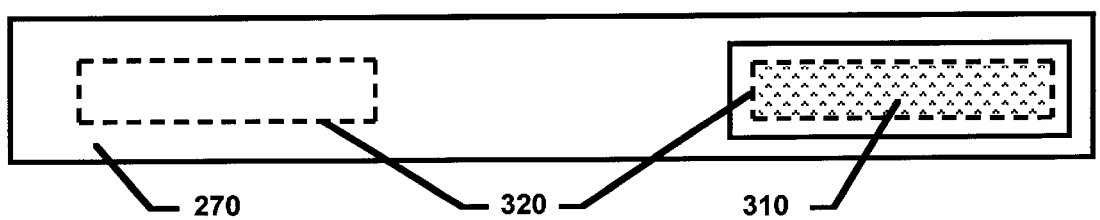
FIG. 7B shows the stabilization-strap inward-facing side (adjacent the patient's skin).
Figure 7C:
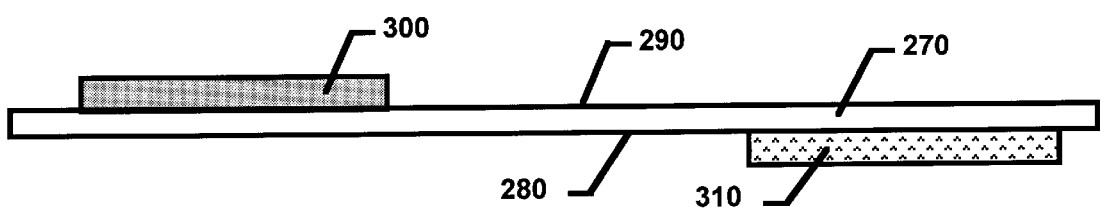
FIG. 7C shows a side view of the stabilization strap.

The stabilization strap 270 is structured similarly to the waist strap 220. A stabilization-strap self-fastening means attaches a first end of the stabilization strap 270 to a second end of the stabilization strap 270. The same options available for use as a waist-strap self-fastening means are available as a stabilization-strap self-fastening means. In the preferred embodiments, hook-and-loop fastener material is used. In the most preferred embodiments (FIG. 7), a stabilization-strap strip of hook material 300 is affixed to the stabilization-strap outward-facing side 290 and stabilization-strap strip of loop material 310 is affixed to the stabilization-strap inward-facing side 280.

The primary strap 120 in the embodiment shown in FIG. 6 differs from the primary strap 120 in the embodiments shown in FIGS. 1, 3, and 4 primarily in that no primary strap self-fastening means is needed nor desirable. In addition, the overall length of the primary strap 120 is less in the embodiment of FIG. 6 than in the embodiments of FIGS. 1, 3, and 4. For most applications the primary strap 120 of the embodiments shown in FIGS. 1, 3, and 4 is simply cut to produce the primary strap 120 of the embodiment shown in FIG. 6. The removed piece of the primary strap 120 is usable as the stabilization strap 270. When this is desired, the removed piece of the primary strap 120 ideally includes a small portion of the primary strap strip of hook material 160 that can serve as the stabilization strap strip of hook material 300. Variants of the receptacle fastener 150 discussed above for the embodiments shown in FIGS. 1, 3, and 4 are also applicable to the embodiment of FIG. 6.

The adjustable support system 100 is well suited for facilitating the sometimes burdensome chore of showering while still having a receptacle 110 attached. The adjustable support system 100 is wearable during a shower, thereby freeing the user's limbs and allowing safer mobility for a user still recovering from surgery or an injury. Upon completing the shower, the user substitutes a clean and dry adjustable support system 100 for the previous one, which can now be laundered.

The hook-and-loop material used in the invention is generally stitched to the appropriate straps, although other means of supporting the hook-and-loop material, such as pinning, clamping, or the use of permanent or non-permanent adhesives are possible. An adhesive is generally used to affix the hook-and-loop material to the receptacle 110, although stitching, pinning, and clamping are alternative methods.

Any suitable material is appropriate for the straps used in the invention. User comfort and a desire for hypoallergenic materials suggest that cotton is a good choice, although nylon straps have worked well.

Although the receptacle 110 in the above-described invention is typically a drainage receptacle, such as a suction reservoir, a bulb reservoir, or a urine drainage bag, any suitably sized and shaped container can be used as the receptacle 110. In particular, intravenous bags that are not in actual use may be supported by the adjustable support system 100 so that the user can ambulate more freely. The term medical receptacle is intended to include intravenous bags, all of the above-mentioned drainage receptacles, and other containers used for medical purposes.

The above description and drawings are only illustrative of preferred embodiments which achieve the objects, features and advantages of the present invention, and it is not intended that the present invention be limited thereto. Any modification of the present invention that comes within the spirit and scope of the following claims is considered part of the present invention.

What is claimed is:

1. An adjustable support system for a medical receptacle consisting of:
   a primary strap having an inward-facing side and an outward-facing side, wherein the primary strap is adapted to be draped along a path extending over a shoulder of the user and around the user's trunk;
   a primary strap strip of hook material secured to a portion of the outward-facing side of the primary strap;
   a primary strap strip of loop material secured to a portion of the inward-facing side of the primary strap wherein a portion of the primary strap strip of loop material adjustably engages a portion of the primary strap strip of hook material capable of, forming a closed loop around the user's trunk; and
   a suction reservoir having a strip of loop material secured thereto wherein the loop material of the suction reservoir engages the primary strap strip of hook material.

2. An adjustable support system for a medical receptacle consisting of:
   a primary strap for supporting a suction reservoir wherein the primary strap has an inward-facing side and an outward-facing side, wherein the primary strap is adapted to be draped along a path extending over a shoulder of the user and around the user's trunk, and wherein the primary strap has a waist-strap loop having a waist strap passing therethrough, wherein the waist strap has an inward-facing side and an outward-facing side, wherein a waist strap strip of hook material capable of is attached to a portion of the outward-facing side of the waist strap and wherein a waist strap strip of loop material is attached to a portion of the inward-facing side of the waist strap, wherein a portion of the waist strap strip of loop material adjustably engages a portion of the waist strap strip of hook material forming a closed loop around the user's waist;
   a primary strap strip of hook material secured to a portion of the outward-facing side of the primary strap;
   a primary strap strip of loop material secured to a portion of the inward-facing side of the primary strap wherein a portion of the primary strap strip of loop material adjustably engages a portion of the primary strap strip of hook material capable of, forming a closed loop around the user's trunk; and
   a suction reservoir having a strip of loop material secured thereto wherein the loop material of the suction reservoir engages the primary strap strip of hook material.

* * * * *